United States Patent
Cameron et al.

(10) Patent No.: US 9,443,736 B2
(45) Date of Patent: Sep. 13, 2016

(54) SILYLENE COMPOSITIONS AND METHODS OF USE THEREOF

(71) Applicant: ENTEGRIS, INC., Billerica, MA (US)

(72) Inventors: Thomas M. Cameron, Newtown, CT (US); Susan V. DiMeo, New City, NY (US); Bryan C. Hendrix, Danbury, CT (US); Weimin Li, New Milford, CT (US)

(73) Assignee: ENTEGRIS, INC., Billerica, MA (US)

( * ) Notice: Subject to any disclaimer, the term of this patent is extended or adjusted under 35 U.S.C. 154(b) by 0 days.

(21) Appl. No.: 14/400,793

(22) PCT Filed: May 22, 2013

(86) PCT No.: PCT/US2013/042296
§ 371 (c)(1),
(2) Date: Nov. 12, 2014

(87) PCT Pub. No.: WO2013/177326
PCT Pub. Date: Nov. 28, 2013

(65) Prior Publication Data
US 2015/0147824 A1 May 28, 2015

Related U.S. Application Data

(60) Provisional application No. 61/652,010, filed on May 25, 2012, provisional application No. 61/732,900, filed on Dec. 3, 2012.

(51) Int. Cl.
*H01L 21/00* (2006.01)
*H01L 21/28* (2006.01)
(Continued)

(52) U.S. Cl.
CPC ........... *H01L 21/28229* (2013.01); *C07F 7/10* (2013.01); *C09D 5/24* (2013.01);
(Continued)

(58) Field of Classification Search
CPC ....... H01L 21/28; H01L 49/02; H01L 29/51; C23C 16/40; C23C 16/44; C23C 16/455; C09D 5/24
See application file for complete search history.

(56) References Cited

U.S. PATENT DOCUMENTS

| 4,915,988 A | 4/1990 | Erbil |
| 4,927,670 A | 5/1990 | Erbil |

(Continued)

FOREIGN PATENT DOCUMENTS

| EP | 0521772 A1 | 1/1993 |
| EP | 0904568 B1 | 4/2001 |

(Continued)

OTHER PUBLICATIONS

Michael Haaf, "Synthesis and Reactivity of a Stable Silylene", J. Am. Chem. Soc. 1998, 120, 12714-12719.*

(Continued)

*Primary Examiner* — Caleb Henry
(74) *Attorney, Agent, or Firm* — Hultquist, PLLC; Steven J. Hultquist; Maggie Chappuis

(57) ABSTRACT

A silicon precursor composition is described, including a silylene compound selected from among: silylene compounds of the formula: wherein each of R and $R^1$ is independently selected from organo substituents; amidinate silylenes; and bis(amidinate) silylenes. The silylene compounds are usefully employed to form high purity, conformal silicon-containing films of $SiO_2$, $Si_3N_4$, SiC and doped silicates in the manufacture of microelectronic device products, by vapor deposition processes such as CVD, pulsed CVD, ALD and pulsed plasma processes. In one implementation, such silicon precursors can be utilized in the presence of oxidant, to seal porosity in a substrate comprising porous silicon oxide by depositing silicon oxide in the porosity at low temperature, e.g., temperature in a range of from 50° C. to 200° C.

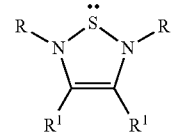

18 Claims, 5 Drawing Sheets

(51) Int. Cl.
    *C07F 7/10*            (2006.01)
    *C23C 16/34*          (2006.01)
    *C23C 16/40*          (2006.01)
    *C09D 5/24*            (2006.01)
    *C23C 16/44*          (2006.01)
    *C23C 16/455*        (2006.01)
    *H01L 49/02*         (2006.01)
    *H01L 29/51*         (2006.01)

(52) U.S. Cl.
    CPC .......... *C23C 16/345* (2013.01); *C23C 16/401* (2013.01); *C23C 16/402* (2013.01); *C23C 16/44* (2013.01); *C23C 16/45525* (2013.01); *H01L 28/40* (2013.01); *H01L 29/516* (2013.01)

(56) References Cited

U.S. PATENT DOCUMENTS

| | | | |
|---|---|---|---|
| 4,948,623 A | 8/1990 | Beach et al. | |
| 4,960,916 A | 10/1990 | Pazik | |
| 4,962,214 A | 10/1990 | Villacorta et al. | |
| 5,204,057 A | 4/1993 | Ishigami et al. | |
| 5,204,141 A | 4/1993 | Roberts et al. | |
| 5,204,314 A | 4/1993 | Kirlin et al. | |
| 5,225,561 A | 7/1993 | Kirlin et al. | |
| 5,280,012 A | 1/1994 | Kirlin et al. | |
| 5,424,095 A | 6/1995 | Clark et al. | |
| 5,453,494 A | 9/1995 | Kirlin et al. | |
| 5,536,323 A | 7/1996 | Kirlin et al. | |
| 5,555,154 A | 9/1996 | Uchikawa et al. | |
| 5,578,530 A | 11/1996 | Muroyama et al. | |
| 5,711,816 A | 1/1998 | Kirlin et al. | |
| 5,744,196 A | 4/1998 | Laxman et al. | |
| 5,770,921 A | 6/1998 | Aoki et al. | |
| 5,820,664 A | 10/1998 | Gardiner et al. | |
| 5,837,417 A | 11/1998 | Rahman et al. | |
| 5,840,897 A | 11/1998 | Kirlin et al. | |
| 5,866,471 A * | 2/1999 | Beppu ................ H01L 31/0322 136/258 | |
| 5,919,522 A | 7/1999 | Baum et al. | |
| 5,939,333 A | 8/1999 | Hurley et al. | |
| 5,990,541 A | 11/1999 | Saito et al. | |
| 6,002,036 A | 12/1999 | Kadokura | |
| 6,013,235 A | 1/2000 | Brinson et al. | |
| 6,024,847 A | 2/2000 | Rosenberg et al. | |
| 6,025,222 A | 2/2000 | Kimura et al. | |
| 6,087,500 A | 7/2000 | Fukuda et al. | |
| 6,110,529 A | 8/2000 | Gardiner et al. | |
| 6,110,531 A | 8/2000 | Paz de Araujo et al. | |
| 6,111,122 A | 8/2000 | Paw et al. | |
| 6,177,558 B1 | 1/2001 | Brennan et al. | |
| 6,218,518 B1 | 4/2001 | Baum et al. | |
| 6,277,436 B1 | 8/2001 | Stauf et al. | |
| 6,297,539 B1 | 10/2001 | Ma et al. | |
| 6,340,386 B1 | 1/2002 | Hendrix et al. | |
| 6,342,445 B1 | 1/2002 | Marsh | |
| 6,383,955 B1 | 5/2002 | Matsuki et al. | |
| 6,410,463 B1 | 6/2002 | Matsuki | |
| 6,440,495 B1 | 8/2002 | Wade et al. | |
| 6,479,100 B2 | 11/2002 | Jin et al. | |
| 6,506,666 B2 | 1/2003 | Marsh | |
| 6,511,706 B1 | 1/2003 | Hendrix et al. | |
| 6,562,678 B1 | 5/2003 | Uchiyama et al. | |
| 6,599,447 B2 | 7/2003 | Stauf et al. | |
| 6,646,122 B1 | 11/2003 | Nuhlen et al. | |
| 6,660,331 B2 | 12/2003 | Hendrix et al. | |
| 6,680,251 B2 | 1/2004 | Won et al. | |
| 6,743,739 B2 | 6/2004 | Shimamoto et al. | |
| 6,787,186 B1 | 9/2004 | Hintermaier | |
| 6,849,122 B1 | 2/2005 | Fair | |
| 6,869,638 B2 | 3/2005 | Baum et al. | |
| 6,936,548 B2 | 8/2005 | Dussarrat et al. | |
| 6,960,538 B2 | 11/2005 | Ahn et al. | |
| 6,984,591 B1 | 1/2006 | Buchanan et al. | |
| 6,989,457 B2 | 1/2006 | Kamepalli et al. | |
| 7,019,159 B2 | 3/2006 | Dussarrat et al. | |
| 7,038,284 B2 | 5/2006 | Haukka et al. | |
| 7,064,083 B2 | 6/2006 | Dussarrat et al. | |
| 7,108,747 B1 | 9/2006 | Leskela et al. | |
| 7,132,723 B2 | 11/2006 | Park et al. | |
| 7,172,792 B2 | 2/2007 | Wang et al. | |
| 7,211,509 B1 | 5/2007 | Gopinath et al. | |
| 7,250,367 B2 | 7/2007 | Vaartstra et al. | |
| 7,285,308 B2 | 10/2007 | Hendrix et al. | |
| 7,300,038 B2 | 11/2007 | Gregg et al. | |
| 7,371,633 B2 | 5/2008 | Lee et al. | |
| 7,393,736 B2 | 7/2008 | Ahn et al. | |
| 7,446,217 B2 | 11/2008 | Wang et al. | |
| 7,508,648 B2 | 3/2009 | Ahn et al. | |
| 7,531,679 B2 | 5/2009 | Wang et al. | |
| 7,579,496 B2 | 8/2009 | Wang et al. | |
| 7,601,860 B2 * | 10/2009 | Wang ................ H01L 21/02271 556/410 | |
| 7,615,830 B2 | 11/2009 | Lim et al. | |
| 7,625,794 B2 | 12/2009 | Ahn et al. | |
| 7,635,441 B2 | 12/2009 | Kadokura et al. | |
| 7,638,074 B2 | 12/2009 | Xu et al. | |
| 7,682,593 B2 | 3/2010 | Robert et al. | |
| 7,713,346 B2 | 5/2010 | Wang et al. | |
| 7,781,605 B2 * | 8/2010 | Wang ................ H01L 21/02271 556/406 | |
| 7,786,320 B2 * | 8/2010 | Wang ................ C07F 7/0025 556/410 | |
| 7,790,629 B2 | 9/2010 | Holme et al. | |
| 7,863,203 B2 * | 1/2011 | Wang ................ C07F 7/10 257/E21.478 | |
| 7,887,883 B2 | 2/2011 | Wang et al. | |
| 7,910,765 B2 | 3/2011 | Wang et al. | |
| 8,034,407 B2 | 10/2011 | Hendrix et al. | |
| 8,092,721 B2 | 1/2012 | Gatineau et al. | |
| 8,206,784 B2 | 6/2012 | Xu et al. | |
| 8,221,852 B2 | 7/2012 | Heys et al. | |
| 8,242,032 B2 | 8/2012 | Wang et al. | |
| 8,455,049 B2 | 6/2013 | Cameron et al. | |
| 8,802,882 B2 * | 8/2014 | Wang ................ H01L 21/02271 556/410 | |
| 9,102,693 B2 * | 8/2015 | Wang ................ H01L 21/02271 | |
| 9,120,825 B2 * | 9/2015 | Tada ................ C07F 7/025 | |
| 9,177,783 B2 * | 11/2015 | Saly ................ H01L 21/02211 | |
| 2001/0048973 A1 | 12/2001 | Sato et al. | |
| 2002/0004266 A1 | 1/2002 | Hashimoto et al. | |
| 2002/0067917 A1 | 6/2002 | Takamatsu et al. | |
| 2002/0090815 A1 | 7/2002 | Koike et al. | |
| 2002/0146513 A1 | 10/2002 | Jin et al. | |
| 2003/0012876 A1 | 1/2003 | Min et al. | |
| 2003/0020122 A1 | 1/2003 | Joo et al. | |
| 2003/0032238 A1 | 2/2003 | Kim et al. | |
| 2003/0038594 A1 | 2/2003 | Seo et al. | |
| 2003/0072882 A1 | 4/2003 | Niinisto et al. | |
| 2003/0129306 A1 | 7/2003 | Wade et al. | |
| 2003/0129826 A1 | 7/2003 | Werkhoven et al. | |
| 2003/0165615 A1 | 9/2003 | Aaltonen et al. | |
| 2003/0205823 A1 | 11/2003 | Leu et al. | |
| 2004/0038808 A1 | 2/2004 | Hampden-Smith et al. | |
| 2004/0043149 A1 * | 3/2004 | Gordon ................ C07F 9/091 427/255.31 | |
| 2004/0096582 A1 * | 5/2004 | Wang ................ C07F 7/025 427/255.27 | |
| 2004/0121085 A1 | 6/2004 | Wang et al. | |
| 2004/0138489 A1 | 7/2004 | Wang et al. | |
| 2004/0146644 A1 | 7/2004 | Xiao et al. | |
| 2004/0166671 A1 | 8/2004 | Lee et al. | |
| 2004/0173918 A1 | 9/2004 | Kamal et al. | |
| 2004/0194706 A1 | 10/2004 | Wang et al. | |
| 2004/0197946 A1 | 10/2004 | Vaartstra et al. | |
| 2004/0211998 A1 | 10/2004 | Paz de Araujo et al. | |
| 2004/0214354 A1 | 10/2004 | Marsh et al. | |
| 2004/0224087 A1 | 11/2004 | Weimer et al. | |
| 2005/0009320 A1 | 1/2005 | Goundar | |
| 2005/0009325 A1 | 1/2005 | Chung et al. | |
| 2005/0080285 A1 | 4/2005 | Wang et al. | |
| 2005/0080286 A1 * | 4/2005 | Wang ................ H01L 21/02271 556/410 | |

(56) References Cited

U.S. PATENT DOCUMENTS

| | | |
|---|---|---|
| 2005/0153073 A1 | 7/2005 | Zheng et al. |
| 2005/0186341 A1 | 8/2005 | Hendrix et al. |
| 2005/0208699 A1 | 9/2005 | Furkay et al. |
| 2005/0217575 A1 | 10/2005 | Gealy et al. |
| 2005/0277780 A1* | 12/2005 | Gordon .................. C07F 9/091 556/57 |
| 2006/0006449 A1 | 1/2006 | Jeong et al. |
| 2006/0027451 A1 | 2/2006 | Park et al. |
| 2006/0035462 A1 | 2/2006 | Millward |
| 2006/0049447 A1 | 3/2006 | Lee et al. |
| 2006/0076609 A1 | 4/2006 | Chindalore et al. |
| 2006/0115595 A1 | 6/2006 | Shenai-Khatkhate et al. |
| 2006/0118968 A1 | 6/2006 | Johnston et al. |
| 2006/0128150 A1 | 6/2006 | Gandikota et al. |
| 2006/0138393 A1 | 6/2006 | Seo et al. |
| 2006/0172067 A1 | 8/2006 | Ovshinsky et al. |
| 2006/0172083 A1 | 8/2006 | Lee et al. |
| 2006/0180811 A1 | 8/2006 | Lee et al. |
| 2006/0223931 A1 | 10/2006 | Park et al. |
| 2006/0244100 A1 | 11/2006 | Ahn et al. |
| 2006/0275545 A1 | 12/2006 | Yoshinaka et al. |
| 2007/0026608 A1 | 2/2007 | Choi et al. |
| 2007/0054487 A1 | 3/2007 | Ma et al. |
| 2007/0116888 A1 | 5/2007 | Faguet |
| 2007/0154637 A1 | 7/2007 | Shenai-Khatkhate et al. |
| 2007/0190362 A1 | 8/2007 | Weidman |
| 2007/0262715 A1 | 11/2007 | Yan et al. |
| 2007/0299274 A1* | 12/2007 | Meiere .................. C07F 7/025 556/407 |
| 2008/0118731 A1 | 5/2008 | Srinivasan et al. |
| 2008/0141937 A1 | 6/2008 | Clark |
| 2008/0160174 A1 | 7/2008 | Wang et al. |
| 2008/0193642 A1 | 8/2008 | Yoon et al. |
| 2008/0199975 A1 | 8/2008 | Park et al. |
| 2008/0230854 A1 | 9/2008 | Clark |
| 2008/0241555 A1 | 10/2008 | Clark |
| 2008/0242097 A1 | 10/2008 | Boescke et al. |
| 2008/0242111 A1 | 10/2008 | Holme et al. |
| 2008/0254218 A1 | 10/2008 | Lei et al. |
| 2008/0254232 A1 | 10/2008 | Gordon et al. |
| 2008/0317972 A1 | 12/2008 | Hendriks et al. |
| 2009/0001618 A1 | 1/2009 | Kadokura et al. |
| 2009/0002917 A1 | 1/2009 | Kil et al. |
| 2009/0004383 A1 | 1/2009 | Kadokura et al. |
| 2009/0074965 A1 | 3/2009 | Xu et al. |
| 2009/0084288 A1 | 4/2009 | Wang et al. |
| 2009/0087561 A1 | 4/2009 | Chen et al. |
| 2009/0136658 A1 | 5/2009 | Yoshinaka et al. |
| 2009/0215225 A1 | 8/2009 | Stender et al. |
| 2009/0275164 A1 | 11/2009 | Chen et al. |
| 2009/0321733 A1 | 12/2009 | Gatineau et al. |
| 2010/0015800 A1 | 1/2010 | Hara et al. |
| 2010/0062150 A1 | 3/2010 | Xu et al. |
| 2010/0095865 A1 | 4/2010 | Xu et al. |
| 2010/0112211 A1 | 5/2010 | Xu et al. |
| 2010/0215842 A1* | 8/2010 | Chen ..................... C07F 9/005 427/96.8 |
| 2010/0270508 A1 | 10/2010 | Xu et al. |
| 2010/0291299 A1 | 11/2010 | Cameron et al. |
| 2010/0314590 A1 | 12/2010 | Wang et al. |
| 2011/0136343 A1 | 6/2011 | Wang et al. |
| 2011/0165762 A1 | 7/2011 | Wang et al. |
| 2011/0183528 A1 | 7/2011 | Wang et al. |
| 2011/0195188 A1 | 8/2011 | Hendrix et al. |
| 2012/0064719 A1 | 3/2012 | Lubguban, Jr. et al. |
| 2012/0127629 A1 | 5/2012 | Roeder et al. |
| 2012/0141675 A1 | 6/2012 | Xu et al. |
| 2012/0156894 A1 | 6/2012 | Wang et al. |
| 2012/0178267 A1 | 7/2012 | Wang et al. |
| 2013/0122722 A1 | 5/2013 | Cissell et al. |
| 2013/0251918 A1 | 9/2013 | Cameron et al. |
| 2014/0295071 A1 | 10/2014 | Xu et al. |
| 2014/0329011 A1 | 11/2014 | Wang et al. |

FOREIGN PATENT DOCUMENTS

| | | |
|---|---|---|
| EP | 1441042 A1 | 7/2004 |
| EP | 1149934 B1 | 8/2005 |
| EP | 1645656 A1 | 4/2006 |
| EP | 1798307 A1 | 6/2007 |
| EP | 2000561 A1 | 12/2008 |
| FR | 2693204 A1 | 1/1994 |
| JP | 2-225317 A | 9/1990 |
| JP | 7-70747 A | 3/1995 |
| JP | 7-249616 A | 9/1995 |
| JP | 08-22986 A | 1/1996 |
| JP | 10-125237 A | 5/1998 |
| JP | 10-273779 A | 10/1998 |
| JP | 2000-80476 A | 3/2000 |
| JP | 2002-525426 A | 8/2002 |
| JP | 2003-526219 A | 9/2003 |
| JP | 2004-527651 A | 9/2004 |
| JP | 2004-300152 A | 10/2004 |
| JP | 2005-512323 A | 4/2005 |
| JP | 2006-37123 A | 2/2006 |
| KR | 20010056446 A | 7/2001 |
| KR | 20010088207 A | 9/2001 |
| KR | 10-0443350 B1 | 7/2004 |
| KR | 1020040100766 A | 12/2004 |
| KR | 1020060097807 A | 9/2006 |
| KR | 10-2008-0079514 A | 9/2008 |
| SU | 768457 A | 10/1980 |
| TW | 200912030 A | 3/2009 |
| WO | 0015865 A1 | 3/2000 |
| WO | 0166834 A2 | 9/2001 |
| WO | 03046253 A1 | 6/2003 |
| WO | 2004046417 A2 | 6/2004 |
| WO | 2006012052 A2 | 2/2006 |
| WO | 2006132107 A1 | 12/2006 |
| WO | 2007064376 A2 | 6/2007 |
| WO | 2008088563 A2 | 7/2008 |
| WO | 2008117582 A1 | 10/2008 |
| WO | 2008128141 A2 | 10/2008 |
| WO | 2009020888 A1 | 2/2009 |
| WO | 2010123531 A1 | 10/2010 |
| WO | 2012177642 A2 | 12/2012 |

OTHER PUBLICATIONS

Micheal Haaf, Stable Silylenes, Organosilicon Research Center, Department of Chemistry, Acc. Chem. Res. 2000, 33, 704-714.*

Nicholas J. Hill, "Recent developments in the chemistry of stable silylenes", Journal of Organometallic Chemistry, vol. 689, Issue 24, Nov. 29, 2004, pp. 4165-4183.*

Heinicke J., et al., "Aminosubstituted disilanes: Synthesis by unsymmetrical and symmetrical reductive coupling", "Heteroatom Chem.", 1998, pp. 311-316, vol. 9, No. 3.

Holme, T., et al., "Atomic Layer Deposition and Chemical Vapor Deposition Precursor Selection Method Application to Strontium and Barium Precursors", "J. Phys. Chem.", Jul. 27, 2007, pp. 8147-8151, vol. 111, No. 33.

Huppmann, F., et al., "Reaktionen subvalenter Verbindungen des Siliciums mit alkylierten Aromaten", "Journal of Organometallic Chemistry", 1994, pp. 217-228 (English Abstract), vol. 483.

Kirlin, P., et al., "Thin Films of Barium Fluoride Scintillator Deposited by Chemical Vapor Deposition", "Nuclear Instruments and Methods in Physics Research", 1990, pp. 261-264, vol. A289.

Kirlin, P., et al., "Growth of High Tc YBaCuO Thin Films by Metalorganic Chemical Vapor Deposition", "SPIE", 1989, pp. 115-127, vol. 1187.

Kosola, A., et al., "Effect of annealing in processing of strontium titanate thin films by ALD", "Applied Surface Science", 2003, pp. 102-112, vol. 211.

Kvyatkovskii, O., "On the Nature of Ferroelectricity in Sr1-xAxTiO3 and KTa1-xNbxO3 Solid Solutions", "Physics of the Solid State", 2002, pp. 1135-1144, vol. 44, No. 6.

Lee, G., et al., "Bis[bis(trimethylsilyl)amino]silylene, an Unstable Divalent Silicon Compound", "J. Am. Chem. Soc.", Jul. 9, 2003, pp. 8114-8115, vol. 125, No. 27.

(56) References Cited

OTHER PUBLICATIONS

Leskela, M., et al., "Atomic layer deposition chemistry: recent developments and future challenges", "Angew. Chem. Int. Ed.", Nov. 24, 2003, pp. 5548-5554, vol. 42, No. 45.

Lu, H., et al., "Evolution of itinerant ferromagnetism in SrxPb1-xRuO3 (0 less than or equal to x less than or equal to 1): Interplay between Jahn-Teller distortion and A-site disorder", "Applied Physics Letters", Mar. 22, 2011, pp. 13, vol. 98, No. 122503.

MaComber, D., et al., "(n5-Cyclopentadienyl)- and (n5-Pentamethylcyclopentadienyl)copper Compounds Containing Phosphine, Carbonyl, and n2-Acetylenic Ligands", "J. Am. Chem. Soc.", 1983, pp. 5325-5329, vol. 105.

McCormick, M., et al., "Solution Synthesis of Calcium, Strontium, and Barium Metallocenes", "Polyhedran", 1988, pp. 725-730, vol. 7, No. 9.

Mitzel, N., "Simple silylhydrazines as models for Si-N beta-donor interactions in SiNN units", "Chem. Eur. J.", 1998, pp. 692-698, vol. 4, No. 4.

Niinistoe, J., et al., "Atomic Layer Deposition of High-k Oxides of the Group 4 Metals for Memory Applications", "Advanced Engineering Materials", Mar. 9, 2009, pp. 223-234, vol. 11, No. 4.

Papadatos, F., et al., "Characterization of Ruthenium and Ruthenium Oxide Thin Films deposited by Chemical Vapor Deposition for CMOS Gate Electrode Applications", "Mat. Res. Soc. Symp. Proc.", 2003, pp. N3.3.1-N3.3.6, vol. 745.

Rakhlin, V., et al., "Organosilicon Derivatives of 1,1-Dimethylhydrazine: Novel Precursors of Thin-Film Dielectric Coatings", "Doklady Chemistry", Feb. 2003, pp. 47-49, vol. 388, No. 4-6.

Ren, H., et al., "Synthesis and structures of cyclopentadienyl N-heterocyclic carbene copper(I) complexes", "Journal of Organometallic Chemistry", Jun. 21, 2006, pp. 4109-4113, vol. 691.

Scherer, O., et al., "Chemical Abstract 1965:439205, Ethylenimine and imidazolidinone derivatives of silicon", "Chemische Berichte", 1965, pp. 2243-2247, vol. 98, No. 7.

Schuh, H., et al., "Disilanyl-Amines-Compounds Comprising the Structural Unit Si-Si-N, as Single Source Precursors for Plasma-Enhanced Chemical Vapour Deposition (PE-CVD) of Silicon Nitride", "Z. anorg. allg. Chem.", 1993, pp. 1347-1352 (English Abstract), vol. 619.

Selg, P., et al., "Solution Infrared Spectroscopic Studies on Equilibrium Reactions of Co With the Decamethylmetallocenes CP2MII, Where M=Mg, Ca, Sr, Ba, Sm, Eu, Yb", "Organometallics", Jun. 22, 2002, pp. 3100-3107, vol. 21, No. 15.

Sergeeva, Z., et al, "Chemical Abstract 1959:62140; Synthesis of 1,1-dialkyl-2-(trialkylsilyl)hydrazines", "Khim. i Prakt. Primenenie Kremneorg. Soedinenii", 1958, pp. 235-241, vol. 1.

Sergeeva, Z., et al, "Chemical Abstract 1960:127948, Synthesis of alkyl- and dialkylbis(1,1-dialkylhydrazino) Manes", "Zhurnal Obshceii Khimii", 1960, pp. 694-695, vol. 30.

Sergeeva, Z., et al, "Chemical Abstract 1963:27415, A new method of synthesis of organosilicon hydrazines", "Zhurnal Obshchei Khimii", 1962, pp. 1987-1993, vol. 32.

Sergeeva, Z., et al, "Chemical Abstract 1963:455-161, Reaction of nonsymmetric dialkylhydrazines with alkylchloro-silanes", "Zhurnal Obshchei Khimii", 1963, pp. 1874-1878, vol. 33, No. 6.

Singh, R., et al., "In-Situ Processing of Epitaxial Y-Ba-Cu-O High Tc Superconducting Films on (100) SrTiO3 and (100) YS-ZrO2 Substrates at 500-650 Degrees Celsius", "Applied Physics Letters", May 29, 1989, pp. 2271-2273, vol. 54, No. 22.

Smirnova, T., et al., "Plasma-enhanced chemical vapor deposition of silicon carbonitride films from volatile silyl derivatives of 1,1-Dimethylhydrazine", "High Energy Chemistry", Sep. 16-21, 2002, pp. 303-309 (2003), vol. 37, No. 5, Publisher: Proceedings of the 3rd International Symposium on Theoretical and Applied Plasma Chemistry, Ples, Russia.

Smirnova, T., et al., "SiCN alloys obtained by remote plasma chemical vapour deposition from novel precursors", "Thin Solid Films", Apr. 1, 2003, pp. 144-151, vol. 429, No. 1-2.

Smirnova, T., et al., "Composition and Structure of films deposited from silyl derivatives of assymetrical dimthylhydrazine", "Inorganic Materials", Feb. 2003, pp. 117-122, vol. 39, No. 2.

Smirnova, T., et al., "Microstructure and Chemical Bonding in Silicon Carbonitride Films Synthesized by Plasma Enhanced Chemical Vapor Deposition", "Journal of Structural Chemistry", Jan. 2003, pp. 169-173, vol. 44, No. 1.

Soeldner, M., et al., "1,2-Disilanediyl Bis(triflate), F3CSO3-SiH2SiH2-O3SCF3, as the Key Intermediate for a Facile Preparation of Open-Chain and Cyclic 1,1- and 1,2-Diaminodisilanes", "Inorg. Chem.", Apr. 23, 1997, pp. 1758-1763, vol. 36, No. 9.

University of Minnesota, "The Transition Metals", Accessed via internet Jan. 2014, pp. 1-44.

Vehkamaki, M., et al., "Growth of SrTiO3 and BaTiO3 Thin Films by Atomic Layer Deposition", "Electrochemical Solid-State Letters", Aug. 5, 1999, pp. 504-506, vol. 2, No. 10.

Vehkamaki, M., et al., "Atomic Layer Deposition of SrTiO3 Thin Films from a Novel Strontium Precursor-Strontium-bis(triisopropylcyclopentadienyl)", "Chemical Vapor Deposition", Mar. 2001, pp. 75-80, vol. 7, No. 2.

Voronkov, M., et al., "Silyl derivatives Unsymmetrical dimethylhydrazine as Reagents for Synthesis of Composite Structures in Layers in Silicon", "Materialy Elektronnoi Tekhniki (Month of Publication Not Currently Determinable)", 2002, pp. 57-60 (Machines Translation English Abstract), vol. 4.

Wan, Y., et al., "Synthesis of (dialkylamino)disilanes", "Inorg. Chem.", Feb. 3, 1993, pp. 341-344, vol. 32, No. 3.

Wannagat, U., et al., "Chemical Abstract 1959:93473, Hydrazine-silicon compounds II Mixed alkyl-or aryl-substituted hydrazines", "Z. anorg. u allgem. Chem.", 1959, pp. 341-348, vol. 299.

Wannagat, U., et al., "Chemical Abstract 1966:104351, Si-N compounds. LIII. Si-N2H4 compounds. 7. Some new hyrdazinosilanes", "Monatshefte fuer Chemie", 1965, pp. 1902-1908, vol. 96, No. 6.

Wannagat, U., et al., "Chemical Abstract 1967:18737, Silicon-Nitrogen compounds. LXI. Silicaon-hydrazine compounds. 11. Hypergolity of silylhydrazines", "Monatshefte fuer Chemie", 1966, pp. 1157-1162, vol. 97, No. 4.

West, R., et al., "Tetramesityldisilene, a Stable Compound Containing a Silicon-Silicon Double Bond", "Science", Dec. 18, 1981, pp. 1343-1344, vol. 214, No. 4527.

West, R., et al., "Stable silylenes: Synthesis, structure, reactions", "Pure & Appl. Chem.", 1996, pp. 785-788, vol. 68, No. 4.

West, R., et al., "Chemical Shift Tensors and NICS Calculations for Stable Silylenes", "J. Am. Chem. Soc.", Feb. 5, 1998, pp. 1639-1640, vol. 120, No. 7.

"Wikipedia Entry for the term 'Vapor Pressure'", http://en.wikipedia.org/wiki/Vapor_pressure (Accessed on Jul. 17, 2007).

Note: For the non-patent literature citations that no month of publication is indicated, the year of publication is more than 1 year prior to the effective filing date of the present application.

Witte-Abel, H., et al., "Kondensationen von Silylhydrazinen und Estern zu Silylhydrazonen und Pyrazolnen", "J. Organometallic Chem.", Aug. 15, 1999, pp. 341-347 (English Abstract), vol. 585, No. 2.

Wu, L., et al., "Humidity Sensitivity of Sr(Sn, Ti)03 Ceramics", "Journal of Electronic Materials", 1990, pp. 197-200, vol. 19, No. 2.

Yang, J., et al., "Disilane-Catalyzed and Thermally Induced Oligomerizations of Alkynes: A Comparison", "Organometallics", Mar. 6, 2000, pp. 893-900, vol. 19, No. 5.

Yang, J., et al., "Synthesis of 1,4-disilacyclohexa-2,5-dienes", "Journal of Organometallic Chemistry", Apr. 22, 2002, pp. 276-288, vol. 649.

Anderson, Q., et al., "Synthesis and Characterization of the First Pentaphenylcyclopentadienyl Copper(I) Complex, (Ph5Cp)Cu(PPh3)", "Organometallics", 1998, pp. 4917-4920, vol. 17.

Artaud-Gillet, M., et al., "Evaluation of copper organometallic sources for CuGaSe2 photovoltaic applications", "Journal of Crystal Growth", 2003, pp. 163-168, vol. 248.

(56) References Cited

OTHER PUBLICATIONS

Burns, C., et al., "Organometallic Coordination Complexes of the BIS (Pentamethylcyclopentadienyl)-Alkaline Earth Compounds, (ME5C5)2MLN, Where M Is Mg, Ca, Sr, or Ba and ME5C5BECL", "Journal of Organometallic Chemistry", 1987, pp. 31-37, vol. 325.

Chen, L., et al., "Crystalline silicon carbon nitride: A wide band gap semiconductor", "Appl. Phys. Letters.", May 11, 1998, pp. 2463-2465, vol. 72, No. 19.

Christen, H., et al., "Semiconducting epitaxial films of metastable SrRu0.5Sn0.5O3 grown by pulsed laser deposition", "Applied Physics Letters", 1997, pp. 2147-2149 (Title and Abstract), vol. 70, No. 16.

Denk, M., et al., "Synthesis and Structure of a Stable Silylene", "J. Am. Chem. Soc.", Mar. 23, 1994, pp. 2691-2692, vol. 116, No. 6.

Gibson, G., et al., "The Reaction of Silicon Tetrachloride with N,N-Dimethylhydrazine and Hydrazine", "Inorg. Chem.", Aug. 1963, pp. 876-878, vol. 2, No. 4.

Haaf, M., et al., "Synthesis and Reactivity of the Stable Silylene N,N'-Di-Tert-Butyl-1,3-Diaza-2-Sila-2-Ylidene", "Canadian Journal of Chemistry", Nov. 2000, pp. 1526-1533 (Abstract), vol. 78, No. 11.

Hatanpaa, T., et al., "Synthesis and characterisation of cyclopentadienyl complexes of barium: precursors for atomic layer deposition of BaTiO3", "Dalton Trans.", Mar. 22, 2004, pp. 1181-1188, vol. 8.

\* cited by examiner

SILYLENE COMPOSITIONS AND METHODS OF USE THEREOF

CROSS-REFERENCE TO RELATED APPLICATIONS

This application is a U.S. national phase under the provisions of 35 U.S.C. §371 of International Patent Application No. PCT/US13/42296 filed May 22, 2013, which in turn claims the benefit of priority under 35 USC 119 of U.S. Provisional Patent Application No. 61/652,010 filed on May 25, 2012 and the benefit of priority under 35 USC 119 of U.S. Provisional Patent Application No. 61/732,900 filed on Dec. 3, 2012 . The disclosures of such international patent application and U.S. priority provisional patent applications are hereby incorporated herein by reference in their respective entireties, for all purposes.

FIELD

The present disclosure relates to silicon-based films for fabrication of microelectronic devices, and to silicon precursors useful in depositing such films by vapor deposition processes.

DESCRIPTION OF THE RELATED ART

Low temperature deposition of silicon-based thin-films is of fundamental importance to current semiconductor device fabrication and processes. For the last several decades, $SiO_2$ thin films have been utilized as essential structural components of integrated circuits (ICs), including microprocessor, logic and memory based devices. $SiO_2$ has been a predominant material in the semiconductor industry and has been employed as an insulating dielectric material for virtually all silicon-based devices that have been commercialized. $SiO_2$ has been used as an interconnect dielectric, a capacitor and a gate dielectric material over the years.

The conventional industry approach for depositing high-purity $SiO_2$ films has been to utilize tetraethylorthosilicate (TEOS) as a thin-film precursor for vapor deposition of such films. TEOS is a stable, liquid material that has been employed as a silicon source reagent in chemical vapor deposition (CVD), plasma-enhanced chemical vapor deposition (PECVD) and atomic layer deposition (ALD), to achieve high-purity thin-films of $SiO_2$. Other thin-film deposition methods (e.g., focused ion beam, electron beam and other energetic means for forming thin-films) can also be carried out with this silicon source reagent.

As IC device dimensions continually decrease, with corresponding advances in lithography scaling methods and shrinkage of device geometries, new deposition materials and processes are correspondingly being sought for forming high integrity $SiO_2$ thin films. Improved silicon-based precursors (and co-reactants) are desired to form $SiO_2$ films, as well as other silicon-containing thin films, e.g., $Si_3N_4$, SiC, and doped $SiO_x$ high k thin films, that can be deposited at low temperatures, such as temperatures below 400° C., and more preferably below 200° C. To achieve these low deposition temperatures, chemical precursors are required that decompose cleanly to yield the desired films.

The achievement of low temperature films also requires the use and development of deposition processes that ensure the formation of homogeneous conformal silicon-containing films. Chemical vapor deposition (CVD) and atomic layer deposition (ALD) processes are therefore being refined and implemented, concurrently with the ongoing search for reactive precursor compounds that are stable in handling, vaporization and transport to the reactor, but exhibit the ability to decompose cleanly at low temperatures to form the desired thin films. The fundamental challenge in this effort is to achieve a balance of precursor thermal stability and precursor suitability for high-purity, low temperature film growth processes.

In the search for improved silicon precursors, organosilanes such as teramethoxysilane (TMOS), tetrachlorosilane (TCS), hexachlorodisilane (HCDS) and tris(dimethylamido) silane (TDMAS) have been evaluated for ALD deposition of $SiO_2$. Such silicon precursors can be utilized with oxidizing co-reactants, such as $O_2$, $O_3$, $N_2O$, water and Lewis base species to achieve $SiO_2$ thin-films, or with reducing species such as $H_2$ or $NH_3$, to achieve nitride thin-films.

The art continues to seek improvements and new chemistries for vapor deposition of silicon-containing films for manufacture of microelectronic devices.

SUMMARY

The present disclosure relates to silicon precursors useful in depositing silicon-containing films by vapor deposition processes, to films formed using such precursors, and microelectronic devices including such films.

In one aspect, the disclosure relates to silicon precursor composition comprising a silylene compound selected from among:
silylene compounds of the formula:

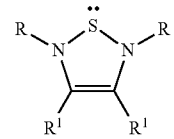

wherein each of R and $R^1$ is independently selected from organo substituents;
amidinate silylenes; and
bis(amidinate) silylenes.

In another aspect, the disclosure relates to a method of forming a silicon-containing film on a substrate, comprising volatilizing a silicon precursor composition of the present disclosure to produce corresponding precursor vapor, and contacting the precursor vapor with the substrate under vapor deposition conditions to form the silicon-containing film on the substrate.

In a further aspect, the disclosure relates to a microelectronic device comprising a silicon-containing film deposited by such method.

A further aspect of the disclosure relates to a silicon-containing film deposited by such method.

The disclosure in a further aspect relates to a method of maintaining amorphous character of an amorphous hafnium oxide or zirconium oxide material during elevated temperature processing thereof, said method comprising incorporating silicon in said amorphous hafnium oxide or zirconium oxide material from a silicon precursor composition of the present disclosure.

Another aspect of the present disclosure relates to a method of making a capacitor, comprising:
forming a bottom electrode;
depositing on the bottom electrode an HfSiO amorphous film by a vapor deposition process, using a silicon precursor composition of the present disclosure, an organohafnium precursor, and an oxic medium in the vapor deposition process; and forming a top electrode on the HfSiO amorphous film.

Yet another aspect of the present disclosure relates to a method of making a ferroelectric field effect transistor, comprising:

forming a base comprising source and drain regions;

depositing on the base, in contact with the source and drain regions, an oxide layer;

forming on the oxide layer a HfSiO material by a vapor deposition process, using a silicon precursor composition of the present disclosure, an organohafnium precursor, and an oxic medium in the vapor deposition process;

depositing a metal-containing layer on the HfSiO material; and annealing the HfSiO material to form ferroelectric HfSiO material.

In another aspect, the disclosure relates to a method of sealing porosity in a substrate comprising porous silicon oxide, comprising volatilizing a silicon precursor of the present disclosure, to produce corresponding precursor vapor, and contacting the precursor vapor with the substrate under vapor deposition conditions including (i) temperature in a range of from 50° C. to 200° C. and (ii) presence of oxidant, to deposit silicon oxide in said porosity of the substrate for sealing thereof.

Other aspects, features and embodiments of the invention will be more fully apparent from the ensuing disclosure and appended claims.

DETAILED DESCRIPTION

Figure 1:
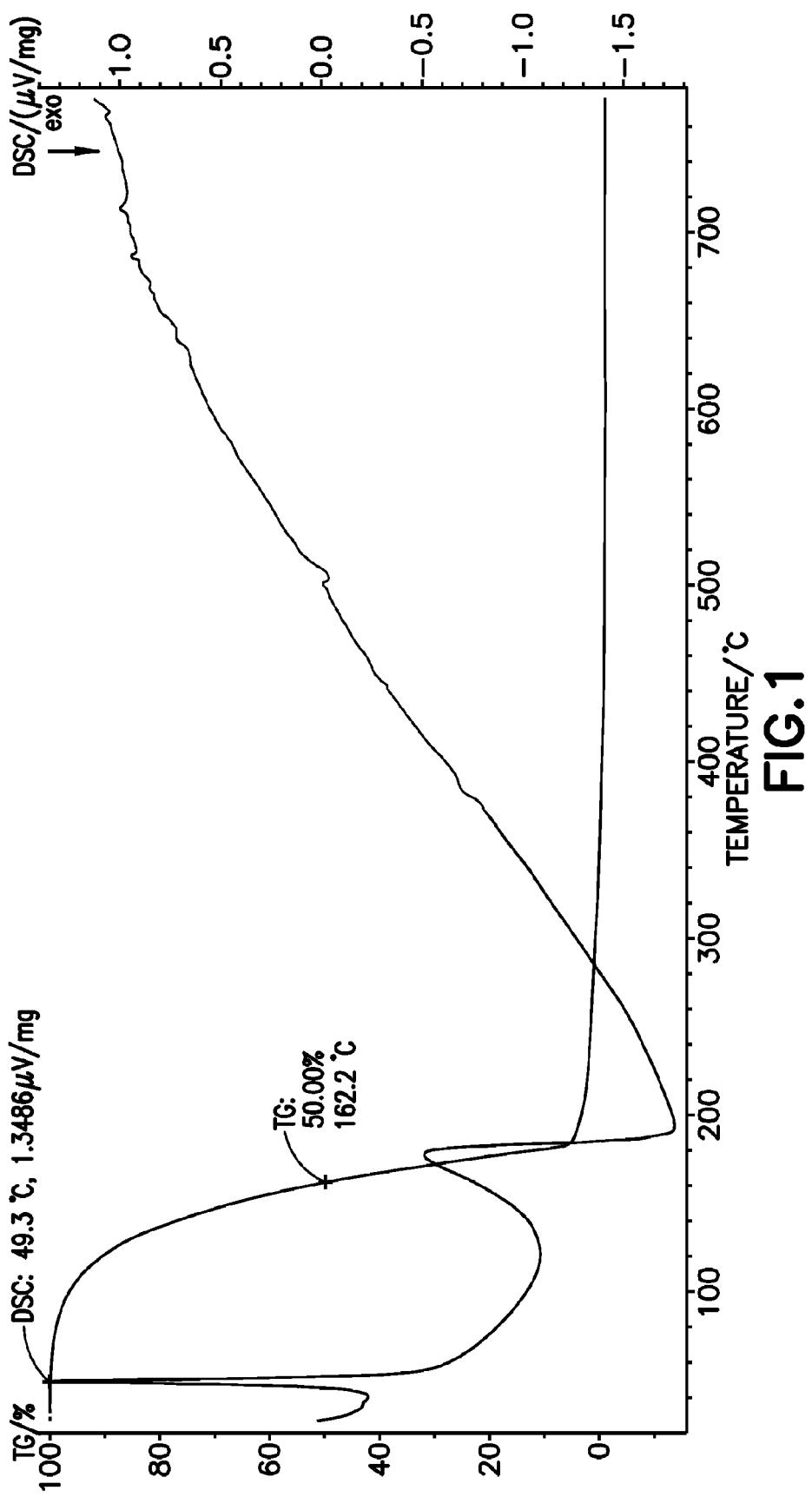
FIG. 1 is a plot of thermogravimetric analysis and differential scanning calorimetry (TG/DSC) data for bis(N-t-amyl)ethylenediamine silylene.

The present disclosure relates to silicon precursors that are amenable to use in low temperature vapor deposition processes such as CVD and ALD, to form silicon-based thin films.

As used herein, the term "film" refers to a layer of deposited material having a thickness below 1000 micrometers, e.g., from such value down to atomic monolayer thickness values. In various embodiments, film thicknesses of deposited material layers in the practice of the invention may for example be below 100, 10, or 1 micrometers, or in various thin film regimes below 200, 100, or 50 nanometers, depending on the specific application involved. As used herein, the term "thin film" means a layer of a material having a thickness below 1 micrometer.

It is noted that as used herein and in the appended claims, the singular forms "a", "and", and "the" include plural referents unless the context clearly dictates otherwise.

As used herein, the identification of a carbon number range, e.g., in $C_1$-$C_{12}$ alkyl, is intended to include each of the component carbon number moieties within such range, so that each intervening carbon number and any other stated or intervening carbon number value in that stated range, is encompassed, it being further understood that sub-ranges of carbon number within specified carbon number ranges may independently be included in smaller carbon number ranges, within the scope of the invention, and that ranges of carbon numbers specifically excluding a carbon number or numbers are included in the invention, and sub-ranges excluding either or both of carbon number limits of specified ranges are also included in the invention. Accordingly, $C_1$-$C_{12}$ alkyl is intended to include methyl, ethyl, propyl, butyl, pentyl, hexyl, heptyl, octyl, nonyl, decyl, undecyl and dodecyl, including straight chain as well as branched groups of such types. It therefore is to be appreciated that identification of a carbon number range, e.g., $C_1$-$C_{12}$, as broadly applicable to a substituent moiety, enables, in specific embodiments of the invention, the carbon number range to be further restricted, as a sub-group of moieties having a carbon number range within the broader specification of the substituent moiety. By way of example, the carbon number range e.g., $C_1$-$C_{12}$ alkyl, may be more restrictively specified, in particular embodiments of the invention, to encompass sub-ranges such as $C_1$-$C_4$ alkyl, $C_2$-$C_8$ alkyl, $C_2$-$C_4$ alkyl, $C_3$-$C_5$ alkyl, or any other sub-range within the broad carbon number range. In other words, a carbon number range is deemed to affirmatively set forth each of the carbon number species in the range, as to the substituent, moiety, or compound to which such range applies, as a selection group from which specific ones of the members of the selection group may be selected, either as a sequential carbon number sub-range, or as specific carbon number species within such selection group.

"Alkyls" as used herein include, but are not limited to, methyl, ethyl, propyl, isopropyl, butyl, s-butyl, t-butyl, pentyl and isopentyl and the like. "Aryls" as used herein includes hydrocarbons derived from benzene or a benzene derivative that are unsaturated aromatic carbocyclic groups of from 6 to 10 carbon atoms. The aryls may have a single or multiple rings. The term "aryl" as used herein also includes substituted aryls. Examples include, but are not limited to phenyl, naphthyl, xylene, phenylethane, substituted phenyl, substituted naphthyl, substituted xylene, substituted phenylethane and the like.

The disclosure, as variously set out herein in respect of features, aspects and embodiments thereof, may in particular implementations be constituted as comprising, consisting, or consisting essentially of, some or all of such features, aspects and embodiments, as well as elements and components thereof being aggregated to constitute various further implementations of the disclosure. The disclosure is described herein in various embodiments, and with reference to various features and aspects. The disclosure contemplates such features, aspects and embodiments in various permutations and combinations, as being within the scope of the present description.

The silicon precursors of the present disclosure are silylene compounds of the formula:

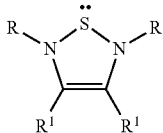

wherein each of R and R¹ is independently selected from organo substituents, e.g., H, $C_1$-$C_{12}$ alkyl, silylalkyl, silylamide, alkylamide, dialkylamide, or aryl. The alkyl moiety in silylalkyl, alkylamide, and dialkylamide substituents may include $C_1$-$C_{12}$ alkyl substituents, and aryl substituents may include any suitable aromatic substituents, including, for example, $C_6$-$C_{15}$ aryl substituents.

The silicon (II) compounds of the above formula enable low-temperature CVD and/or ALD formation of silicon-based thin films such as $SiO_2$ and $Si_3N_4$. Such compounds exhibit high volatility and chemical reactivity, but are stable with respect to thermal degradation at temperatures involved in volatilization of the precursor and transport of the resulting precursor vapor to the deposition chamber. The chemical reactivity of these precursors allows for film growth at low temperatures at which traditional silicon precursor materials such as TEOS are inert and thus exhibit little to no deposition behavior. The thermal stability of these precursors ensures process stability by limiting undesired decomposition of the silylene during delivery and deposition.

The silicon (II) compounds of the present disclosure can be readily synthesized in good yields from common starting materials, within the skill of the art based on the disclosure herein, without undue effort. The substituents R and R¹ in such compounds can be varied to produce a corresponding variety of precursors useful for vapor deposition, e.g., ALD or CVD, with respect to properties such as melting point, thermal stability, and volatility.

An illustrative silicon precursor of the foregoing general formula is bis(N-t-amyl)ethylenediamine silylene:

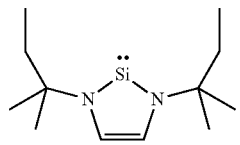

Thermal analysis data are shown in FIG. 1 for such compound, including thermogravimetric analysis and differential scanning calorimetry (TG/DSC) data. The differential scanning calorimetry curve (DSC curve) in the thermal analysis plot in FIG. 1 shows a melting point of 49° C., and the thermogravimetric plot (TG plot) shows efficient thermal transport with a $t_{50}$ value of 162° C. ($t_{50}$ is the temperature corresponding to transport of half of the precursor material). The TG plot also shows a residual mass of less than 1%. Such low residual mass indicates that the compound is stable with respect to thermal degradation at the temperature of the TG determination.

Figure 2:
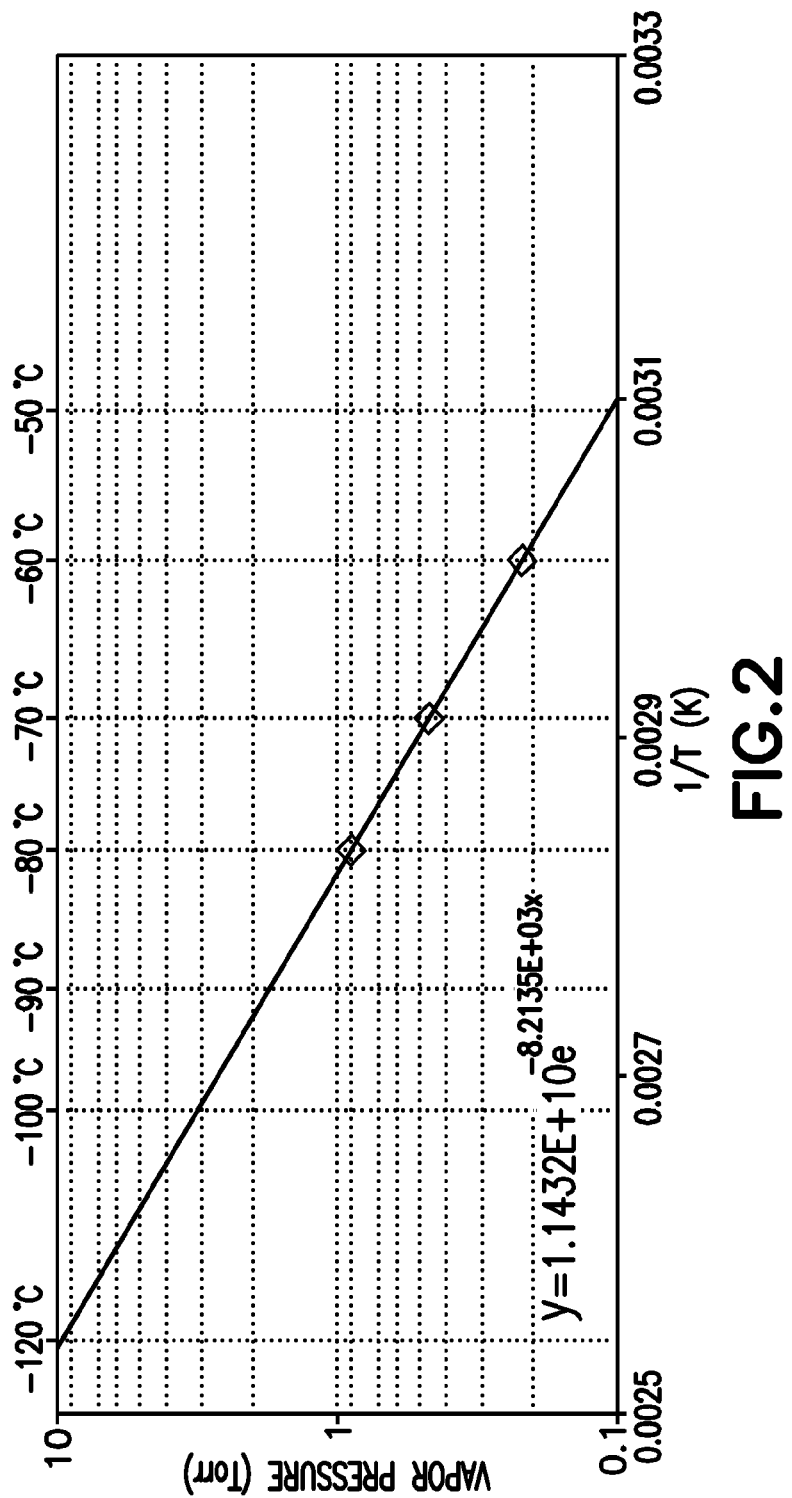
FIG. 2 is a plot of vapor pressure, in torr, as a function of inverse temperature, $1/T(° K)$ for bis(N-t-amyl)ethylenediamine silylene.

FIG. 2 is a plot of vapor pressure, in torr, as a function of inverse temperature, 1/T(° K) for bis(N-t-amyl)ethylenediamine silylene. The vapor pressure was determined by calibrated isothermal weight loss technique, and the data show a vapor pressure of 1 torr (133.3 Pa) at approximately 82° C.

In addition to the foregoing, the thermal stability of bis(N-t-amyl)ethylenediamine silylene has been explored at 160° C., and it has been found that when pure samples of such precursor were heated for 24 hours, no decomposition of the precursor was observable by proton NMR spectroscopy.

Figure 3:
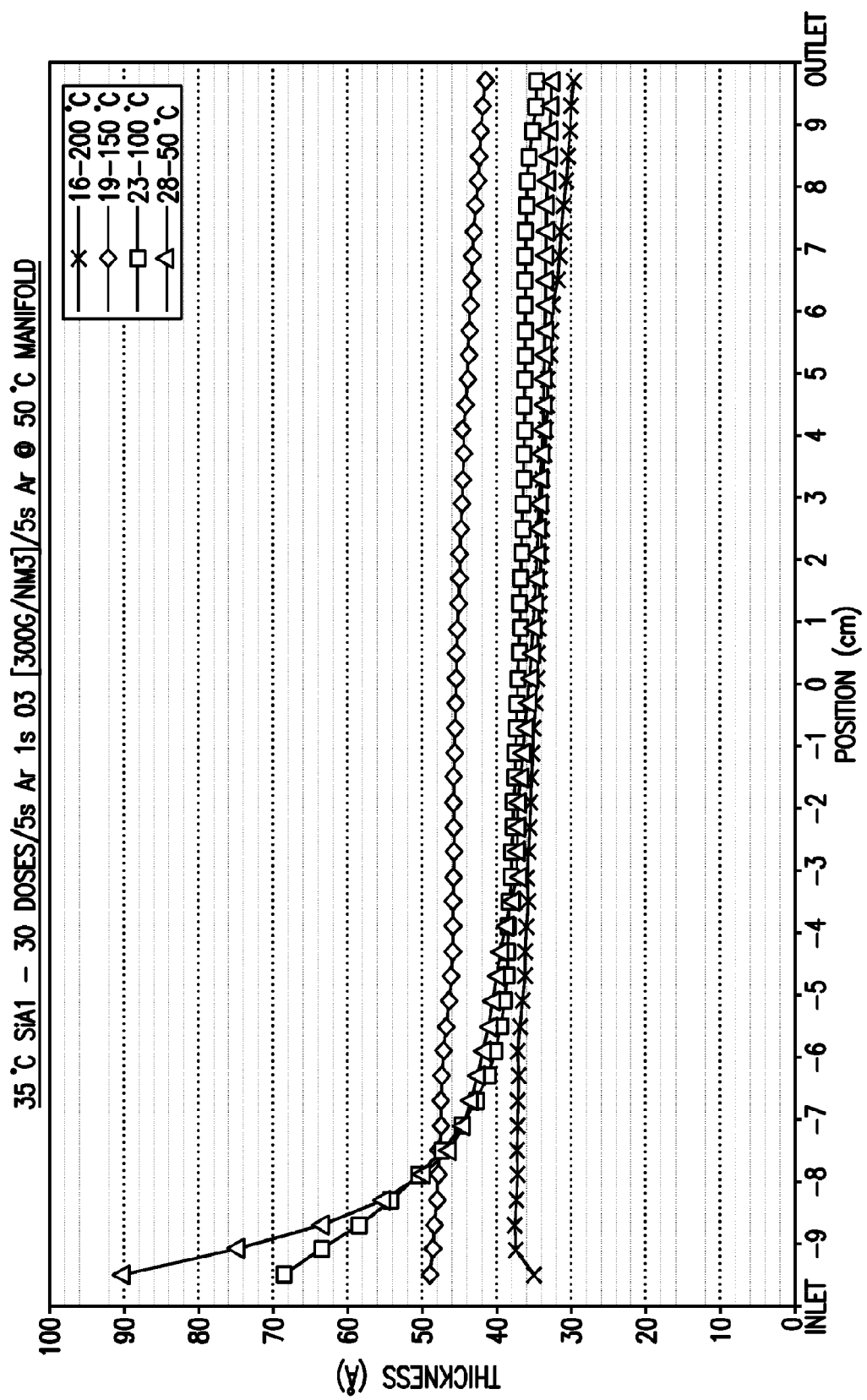
FIG. 3 is a plot of deposited film thickness, in Angstroms, as a function of position, in centimeters, of a silicon oxide film deposited by atomic layer deposition (ALD) using bis(N-t-amyl)ethylenediamine silylene as the silicon precursor.

FIG. 3 is a plot of deposited film thickness, in Angstroms, as a function of position, in centimeters, of the deposited film, for a silicon oxide film deposited by atomic layer deposition (ALD) using bis(N-t-amyl)ethylenediamine silylene as the silicon precursor. 200 ALD cycles were carried out in a cross-flow reactor, with the precursor being supplied from an ampoule maintained at temperature of 35° C., and with 30 boost doses/cycle being provided. 20 wt % ozone was utilized as a co-reactant. The process involved the cycle identified in FIG. 3, as conducted at the specified temperature. The ALD deposition rate was approximately 0.2 Å/cycle at temperature of 50° C.-200° C. The thickness was measured by spectroscopic ellipsometry assuming optical properties of $SiO_2$.

The foregoing reflect the superior character of bis(N-t-amyl)ethylenediamine silylene as a representative precursor composition of the present disclosure. Such compound can be delivered to a deposition reactor at high flux at 82° C. and 1 torr (133.3 Pa) pressure. At a delivery temperature above 49° C., and 1 torr (133.3 Pa) pressure, bis(N-t-amyl)ethylenediamine silylene remains a liquid in the precursor delivery system, thereby facilitating precursor liquid delivery and avoiding the challenges associated with solid delivery techniques. In addition, such compound is resistant to thermal decomposition, thereby ensuring process stability by limiting undesired decomposition of the silylene precursor during delivery and deposition.

To illustrate the broad range of possible precursor compounds of the above-described broad formula, a mixed-ligand silylene precursor, (amidinate bis-trimethylsilylamide) silylene, was synthesized as shown below.

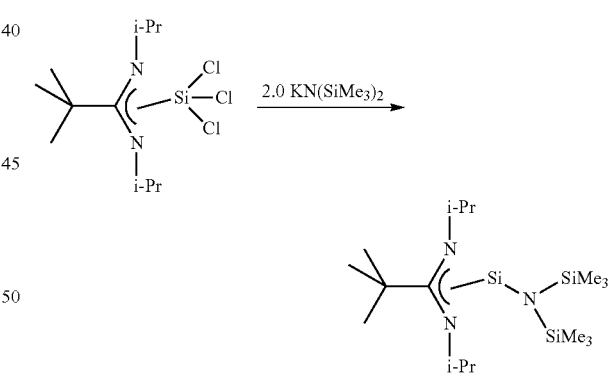

Figure 4:
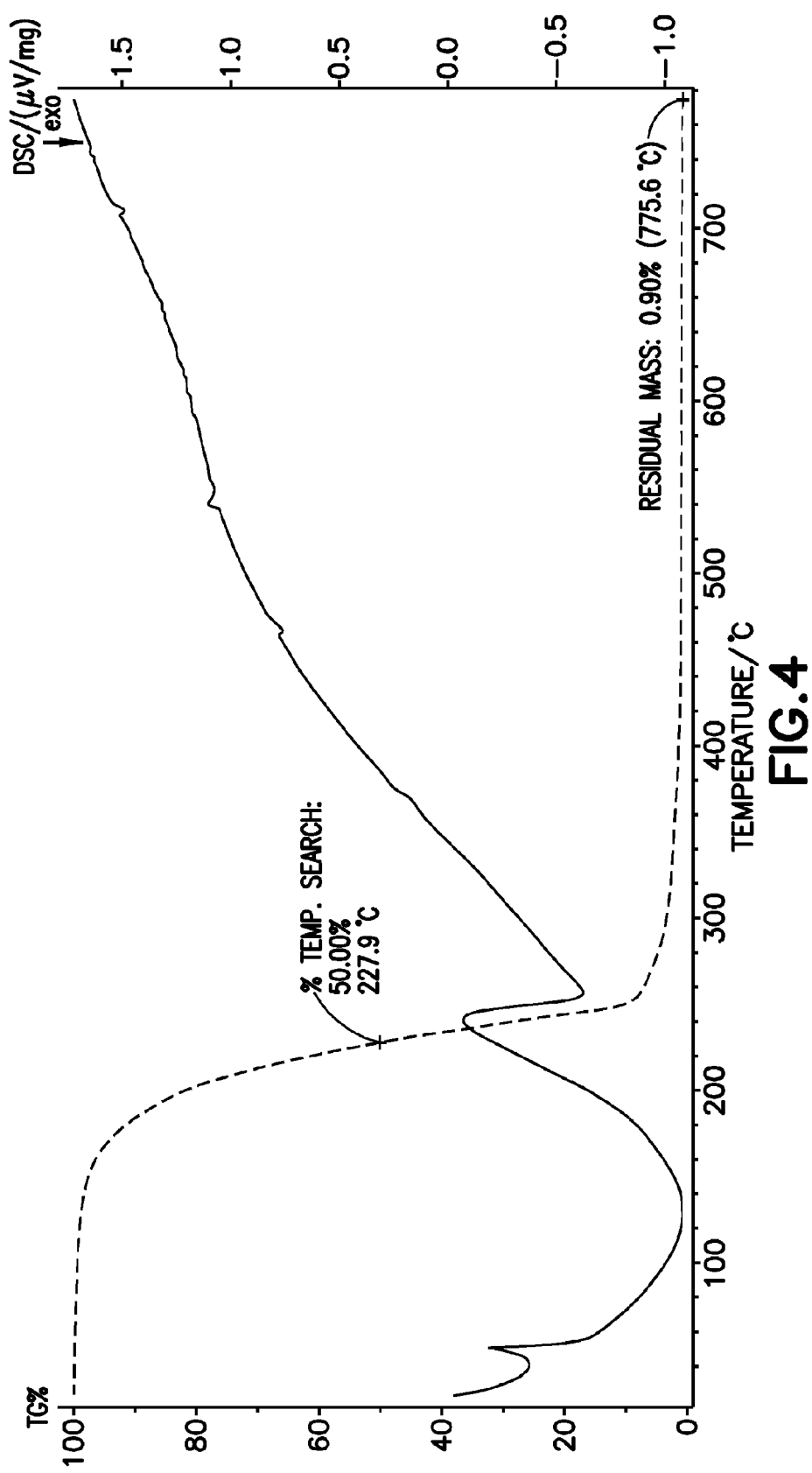
FIG. 4 is a plot of thermogravimetric analysis and differential scanning calorimetry (TG/DSC) data for bis(N-i-propyl)-t-butyl-amidinate bis(trimethylsilyl)amido silylene.

Thermal analysis data for the product bis(N-i-propyl)-t-butyl-amidinate bis(trimethylsilyl)amido silylene are shown in FIG. 4, including thermogravimetric analysis and differential scanning calorimetry (TG/DSC) data. The differential scanning calorimetry curve (DSC curve) in the thermal analysis plot in FIG. 4 shows a melting point of 43° C., and the thermogravimetric plot (TG plot) shows efficient thermal transport with a $t_{50}$ value of 228° C. Bis(N-i-propyl)-t-butyl-amidinate bis(trimethylsilyl)amido silylene thus exhibits good thermal stability and efficient transport characterized by residual mass of less than 1%.

The present disclosure further contemplates bis(amidinate) silylenes of the formula

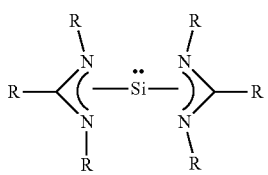

wherein each R is independently selected from organo substituents, e.g., H, $C_1$-$C_{12}$ alkyl, silylalkyl, or silylamide, alkylamide, dialkylamide, or aryl. The alkyl moiety in silylalkyl, alkylamide, and dialkylamide substituents may include $C_1$-$C_{12}$ alkyl substituents, and aryl substituents may include any suitable aromatic substituents, including, for example, $C_6$-$C_{15}$ aryl substituents.

The silylene precursors of the present disclosure can be used to deposit high-purity thin silicon-containing films by any suitable vapor deposition techniques, including, without limitation, CVD, digital CVD, ALD and pulsed plasma processes. Co-reactants can be used to deposit specific thin-film compositions. For example, water, $O_2$, $O_3$ and $N_2O$ can be used to react with the silylene precursors to form $SiO_2$ films. $NH_3$ or alkylamines, e.g., diisopropyl amine, with $H_2$ can be used to form $Si_3N_4$ films. Carbon sources, such as methane or ethane can be used to form SiC films. Doped silicate high k films can be formed, involving co-reaction of the dopant species with the silylene precursors, in an oxidizing environment. Other film growth co-reactants can be readily determined by those skilled in the art of thin-film formation methods, for forming other silicon-containing films within the scope of the present disclosure.

The silylene precursors of the present disclosure can be utilized to form conformal silicon-containing films, such as may be required for high aspect ratio features in microelectronic device substrates, e.g., high-density, high-performance integrated circuit devices. Silicon-containing films thus formed can be used in the fabrication of microprocessor, logic and memory devices in which high-quality thin films are required. Further, the amenability of such silylene precursors to low temperature deposition enables silicon-containing films to be formed and thermally sensitive substrates, such as may be encountered in flexible substrate applications and in the manufacture of flat-panel displays.

Silylene precursors of the present disclosure can be utilized in solid delivery systems, such as those employing solid precursor vaporizers, e.g., vaporizers of the type commercially available from ATMI, Inc. (Danbury, Conn., USA) under the trademark ProE-Vap.

Silylene precursors of the present disclosure can also be dissolved in appropriate organic solvents to facilitate liquid delivery of the precursor into standard as well as specialized deposition reactors.

In general, the silylene precursors can be delivered to microelectronic device substrates for contacting therewith in any suitable manner. In the liquid delivery applications, the use of solvent must be compatible with the silylene precursor, and avoid any deleterious reaction or premature decomposition of the precursor in the delivery and process system.

Thus, the disclosure contemplates silicon precursor compositions comprising a silylene compound selected from among:

silylene compounds of the formula:

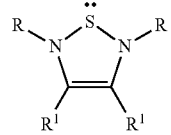

wherein each of R and $R^1$ is independently selected from organo substituents;
amidinate silylenes; and
bis(amidinate) silylenes.

In such silicon precursor compositions, the silylene compound may comprise a compound of the formula:

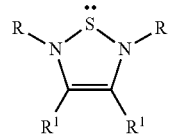

wherein each of R and $R^1$ is independently selected from H, $C_1$-$C_{12}$ alkyl, silylalkyl, silylamide, alkylamide, dialkylamide, and aryl. In one embodiment, the silylene compound comprises bis(N-t-amyl)ethylenediamine silylene.

In another embodiment, the silylene compound may comprise an amidinate silylene, such as bis(N-i-propyl)-t-butyl-amidinate bis(trimethylsilyl)amido silylene.

In a further embodiment, the silylene compound comprises a bis-amidinate silylene, a bis(amidinate) silylene of the formula

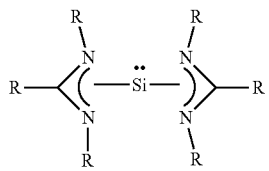

wherein each R is independently selected from organo substituents. In a specific embodiment, each R is independently selected from H, $C_1$-$C_{12}$ alkyl, silylalkyl, silylamide, alkylamide, dialkylamide, and aryl.

The disclosure contemplates a method of forming a silicon-containing film on a substrate, comprising volatilizing a silicon precursor composition of the present disclosure to produce corresponding precursor vapor, and contacting the precursor vapor with the substrate under vapor deposition conditions to form the silicon-containing film on the substrate. The vapor deposition conditions may comprise temperature below 400° C., and preferably comprise temperature in a range of from 50° C. to 200° C.

The silicon-containing film formed in such method may comprise $SiO_2$, or $Si_3N_4$. The contacting conducted in such method may be carried out in a chemical vapor deposition process, or an atomic layer deposition process, and may include a liquid delivery process, a solid delivery process, or other suitable delivery scheme whereby the precursor vapor is delivered to the deposition chamber of a reactor system. The contacting may be carried out with a co-reactant, e.g., an oxic co-reactant selected from the group consisting of water, $O_2$, $O_3$ and $N_2O$, or a nitrogenous co-reactant selected from the group consisting of $NH_3$ and alkylamine/$H_2$ mixtures, or a carbonaceous co-reactant selected from the group consisting of methane and ethane.

Such silicon-containing film formation method may in a specific embodiment for the comprise doping the silicon-containing film. The substrate in the various methods of silicon-containing film formation can comprise a microelectronic substrate, e.g., comprising a high aspect ratio feature on which the silicon-containing film is deposited.

The disclosure further contemplates microelectronic device comprising a silicon-containing film deposited by a method of the present disclosure, and further contemplates silicon-containing films deposited by such method, e.g., comprising $SiO_2$, or $Si_3N_4$.

The disclosure therefore provides silylene precursor compositions as sources for low temperature deposition of high-purity silicon-containing thin films. The silylene precursor compositions may comprise symmetrical or unsymmetrical alkyl substitution, and may include mixed ligands. The silylene precursor compositions of the disclosure enable the formation of silicon containing conformal thin films of high purity character, by techniques including CVD, pulsed CVD, ALD, and pulsed plasma processes. The silicon-containing thin films enabled by the precursors of the present disclosure include thin films of $SiO_2$, $Si_3N_4$, SiC and doped silicates, as used for high k capacitor or gate dielectric films. The silicon-containing films of the disclosure may be deposited on polymeric, plastic or other substrates, in the production of semiconductor products, flat-panel displays, and solar panels.

In various embodiments, the silicon precursors of the disclosure can be used to deposit silicon-containing materials in atomic layer deposition (ALD), chemical vapor deposition (CVD) and pulsed CVD processes, e.g., to deposit silicon-containing films comprising material selected from the group consisting of SiO, SiN, $SiO_2$, SiON, HfSiO, and ZrSiO. In such processes, the silicon precursor may be introduced to the vapor deposition process with a co-reactant such as $NH_3$, $N_2O$, NO, $O_2$, $H_2O$, $O_3$, $H_2O_2$, or the like. Vapor deposition processes utilizing the silicon precursors of the present disclosure can be carried out at low deposition temperatures such as temperature in a range such as from 50° to 400° C., more preferably in a range of from 250° to 380° C., still more preferably in a range of from 280° to 350° C., and most preferably in a range of from 300° to 350° C. It will be appreciated that the properties of the silicon-containing material that is deposited will vary with temperature, and that specific temperatures or temperature ranges can be readily determined within the skill of the art, based on the disclosure herein, for the achievement of specific film properties.

The silicon precursors of the disclosure are usefully employed in various embodiments to incorporate silicon into $HfO_2$ and $ZrO_2$ films. When $ZrCl_4$ and $HfCl_4$ are utilized as precursors with $H_2O$ as a co-reactant to form high k films on semiconductor surfaces without excessive oxidation of the surface at temperatures on the order of 250 to 350° C., $SiCl_4$ has been used to incorporate $SiO_2$ where increased stability to crystallization of the product high k film is desired, but the process of silicon incorporation is difficult to control and the production of chlorine-free films is difficult to achieve in this temperature regime. The silicon precursors of the present disclosure provide an alternative to the use of chlorosilicon precursors and thereby obviate the deficiencies attendant the use of such chlorosilicon precursors in the formation of high k films, particularly in $SiO_2$ vapor deposition processes such as ALD.

The silicon precursors disclosed herein are also useful in the formation of silicon hafnium oxide ferroelectric films, in which small amounts of silicon are incorporated in $HfO_2$ films.

Further, the silicon precursors of the present disclosure are usefully employed to incorporate silicon in hafnium oxide or zirconium oxide films for maintaining amorphous character in such films. For such purpose, an amorphizingly effective amount of silicon is incorporated in the $HfO_2$ or $ZrO_2$ film by deposition from a silylene precursor of the present disclosure. Such incorporation of silicon may for example be carried out in an atomic layer deposition process, utilizing cyclic exposure of a substrate to a silicon precursor of the disclosure, and an organohafnium or organozirconium precursor, as applicable, with ozone or other oxygen-containing gas. The resulting silicon-containing hafnium oxide films or silicon-containing zirconium oxide films are respectively designated herein as HfSiO and ZrSiO films, wherein the corresponding HfSiO and ZrSiO materials may have any suitable stoichiometric constituency appropriate to their end use application.

Thus, the disclosure contemplates methods in which silicon from precursor vapor formed by volatilization of a silicon precursor of the present disclosure is incorporated in $HfO_2$ material on a substrate to form a HfSiO film as a silicon-containing film. Alternatively, silicon from precursor vapor formed by volatilization of a silicon precursor of the present disclosure may be incorporated in $ZrO_2$ material on the substrate to form a ZrSiO film as the silicon-containing film.

In a specific embodiment, the disclosure contemplates a method of maintaining amorphous character of an amorphous hafnium oxide or zirconium oxide material during elevated temperature processing thereof, comprising incorporating silicon in said amorphous hafnium oxide or zirconium oxide material from a silicon precursor composition of the present disclosure.

Methods of forming silicon-containing films are also contemplated, in which vapor deposition conditions comprise performance of an atomic layer deposition process including deposition of silicon from a silicon precursor composition of the disclosure, deposition of hafnium or zirconium from an organohafnium or organozirconium precursor, and exposure to an oxygen-containing gas. The oxygen-containing gas in such methodology may comprise ozone or other suitable oxygen-containing gas.

Figure 5:
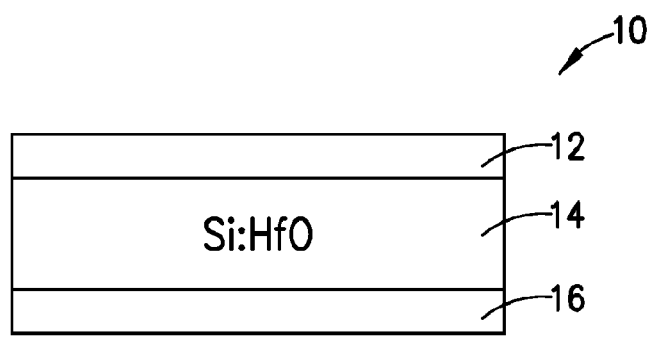
FIG. 5 is a schematic illustration of a metal-insulator-metal capacitor structure utilizing a silicon-containing hafnium oxide film formed using a silicon precursor of the present disclosure.

As a specific example, a capacitor device 10 having a structure as shown in FIG. 5 may be formed by deposition of silicon from the silylene precursor and hafnium from a suitable organohafnium precursor in an oxic environment, to provide an amorphous film of HfSiO 14 on a bottom electrode 16 formed of titanium nitride or other metal composition. A top electrode 12 formed of titanium nitride or other metal composition then may be deposited on the HfSiO film, to constitute the metal-insulator-metal (MIM) capacitor structure that comprises the amorphous HfSiO film, with the capacitor structure then being submitted to elevated temperature annealing, e.g., at temperature in a range of from 500° C. to 1200° C., or more preferably in a range of from 800° C. to 1200° C., to produce a crystalline Si:HfO film in the product capacitor device.

A corresponding generalized method is therefore provided for making a capacitor, comprising:

forming a bottom electrode;

depositing on the bottom electrode an HfSiO amorphous film by a vapor deposition process, using a silicon precursor composition of the disclosure, an organohafnium precursor, and an oxic medium in the vapor deposition process; and forming a top electrode on the HfSiO amorphous film.

Such method may further comprise annealing the HfSiO amorphous film to effect crystallization thereof.

Figure 6:
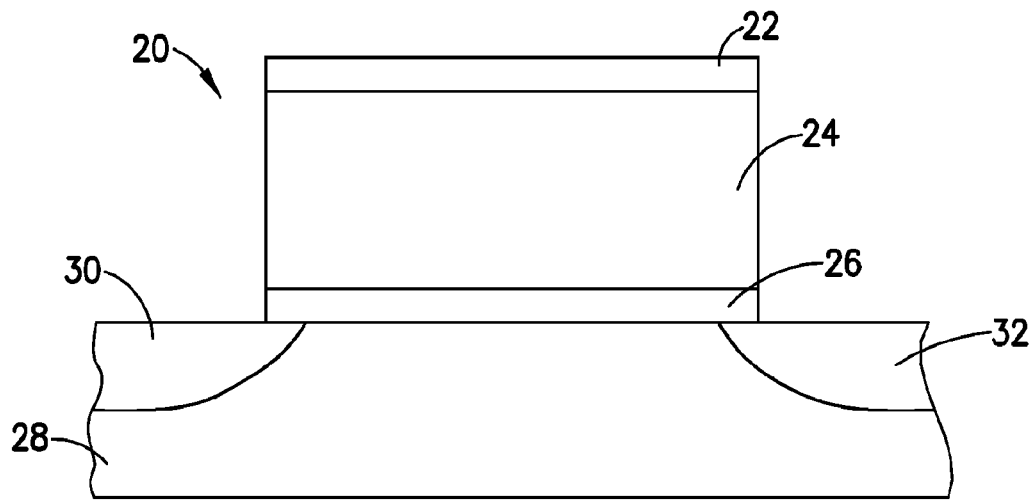
FIG. 6 is a schematic illustration of a ferroelectric field effect transistor (FeFET) incorporating a ferroelectric HfSiO film formed using a silicon precursor of the present disclosure.

In another application, the silylene precursor may be utilized in forming a ferroelectric field effect transistor (FeFET) 20 as illustrated in FIG. 6. Such transistor device includes a base 28 comprising source region 30 and drain region 32, on which is an oxide layer 26, e.g., formed of silicon dioxide ($SiO_2$). Overlying oxide layer 26 is the ferroelectric HfSiO layer 24, capped with a layer 22 of titanium nitride or other metal composition.

In the fabrication of such FeFET device, the ferroelectric HfSiO layer 24 can be formed by vapor deposition process such as chemical vapor deposition or atomic layer deposition, utilizing a silylene precursor of the present disclosure as a silicon source compound, together with an organohafnium precursor, such as tetrakis-dialkylamino hafnium, and ozone or other oxygen containing gas, to effect the formation of the ferroelectric material layer, in which the HfSiO material is in a ferroelectric orthorhombic phase.

FeFET devices of the foregoing type may be utilized in nonvolatile memory applications, in which the nonvolatile memory comprises a multiplicity of such HfSiO FeFETs. The HfSiO films in such FeFETs may be on the order of 3-20 nm, containing a concentration of silicon, measured as Sift, that may for example be in a range of from 1-10 mole percent $SiO_2$ of the HfSiO film. The HfSiO film may be deposited in an amorphous state, and thereafter subjected to elevated temperature annealing, e.g., in a nitrogen ambient, to induce crystallization and formation of the ferroelectric orthorhombic phase, e.g., after deposition of titanium nitride or other electrode material on such film.

Accordingly, a generalized method is provided for making a ferroelectric field effect transistor, comprising:

forming a base comprising source and drain regions;
depositing on the base, in contact with the source and drain regions, an oxide layer;
forming on the oxide layer a HfSiO material by a vapor deposition process, using a silicon precursor composition of the present disclosure, an organohafnium precursor, and an oxic medium in the vapor deposition process;
depositing a metal-containing layer on the HfSiO material; and
annealing the HfSiO material to form ferroelectric HfSiO material.

In such method, the oxide layer may comprise $SiO_2$, the metal-containing layer may comprise TiN, the organohafnium precursor may comprise tetrakis-dialkylamino hafnium, the oxic medium may comprise ozone, and the annealing may be carried out to form the ferroelectric HfSiO material comprising an orthorhombic phase.

In another aspect, silylene precursors of the present disclosure can be utilized for low temperature pore sealing of porous silicon oxide substrates of devices comprising copper-based films such as copper metallization in the device structure. Such use takes advantage of the character of silylenes as high reactivity Si(II) compounds. Silylene precursors of the present disclosure have appropriate volatility characteristics and are usefully employed in deposition processes in which such precursors can react with an activated silicon surface at low temperature to deposit silicon in the form of an oxide when the deposition processes carried out in the presence of an oxidant, e.g., ozone or water. Such oxide deposition may for example be carried out in a non-self-limited film growth mode at temperature in a range of from 50° C. to 200° C., to seal pores in porous silicon networks at low temperatures. This low temperature process is conducted at temperatures that limit damage to copper-based films that are already present in the device structure that comprises the substrate on which the silicon oxide is deposited.

Accordingly, the disclosure contemplates a method of sealing porosity in a substrate comprising porous silicon oxide, comprising volatilizing a silicon precursor composition of the present disclosure to produce corresponding precursor vapor, and contacting the precursor vapor with the substrate under vapor deposition conditions including (i) temperature in a range of from 50° C. to 200° C. and (ii) presence of oxidant, to deposit silicon oxide in said porosity of the substrate for sealing thereof. In such method, the substrate may comprise copper, which as discussed above is benefited by the low temperature character of the porosity-sealing process, and an oxidant such as ozone or water may be employed in the process to enable deposition of silicon oxide as a sealant medium in the substrate porosity.

While the disclosure has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the invention as hereinafter claimed is intended to be broadly construed and interpreted, as including all such variations, modifications and alternative embodiments, within its spirit and scope.

What is claimed is:

1. A silicon precursor composition comprising a silylene compound selected from among:
   (i) silylene compounds of the formula:

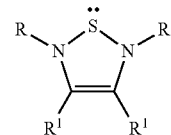

wherein each of R and $R^1$ is independently selected from H, $C_1$-$C_{12}$ alkyl, silylalkyl, silylamide, alkylamide, dialkylamide, and aryl;
   (ii) amidinate silylenes; and
   (iii) bis(amidinate) silylenes,
   wherein when each $R^1$ is H, each R is not butyl, wherein the silylene compound comprises bis (N-t-amyl) ethylenediamine silylene.

2. A silicon precursor composition comprising a silylene compound selected from among:
   (i) silylene compounds of the formula:

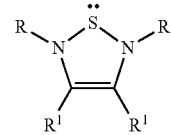

wherein each of R and R¹ is independently selected from
organo substituents,
(ii) amidinate silylenes, and
(iii) bis(amidinate) silylenes,
wherein when each R¹ is H, each R is not butyl, wherein the silylene compound comprises an amidinate silylene.

3. The silicon precursor composition of claim 2, wherein the silylene compound comprises bis (N-i-propyl)-t-butyl-amidinate bis(trimethylsilyl)amido silylene.

4. A silicon precursor composition comprising a silylene compound selected from among:
(i) silylene compounds of the formula:

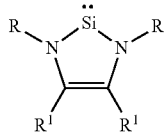

wherein each of R and R¹ is independently selected from
organo substituents,
(ii) amidinate silylenes, and
(iii) bis(amidinate) silylenes,
wherein when each R¹ is H, each R is not butyl,
wherein the silylene compound comprises a bis-amidinate silylene.

5. The silicon precursor composition of claim 4, wherein the bis(amidinate) silylene has the formula

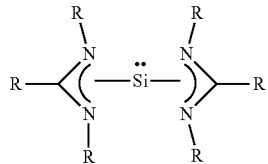

wherein each R is independently selected from organo substituents.

6. The silicon precursor composition of claim 5, wherein each R is independently selected from H, $C_1$-$C_{12}$ alkyl, silylalkyl, silylamide, alkylamide, dialkylamide, and aryl.

7. A method of maintaining amorphous character of an amorphous hafnium oxide or zirconium oxide material during elevated temperature processing thereof, said method comprising incorporating silicon in said amorphous hafnium oxide or zirconium oxide material from a silicon precursor composition comprising a silylene compound selected from among:
(i) silylene compounds of the formula:

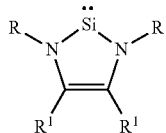

wherein each of R and R¹ is independently selected from
organo substituents,
(ii) amidinate silylenes; and
(iii) bis(amidinate) silylenes,
wherein when each R¹ is H, each R is not butyl.

8. A method of making a capacitor, comprising:
forming a bottom electrode;
depositing on the bottom electrode an HfSiO amorphous film by a vapor deposition process, using a silicon precursor composition, an organohafnium precursor, and an oxic medium in the vapor deposition process; and
forming a top electrode on the HfSiO amorphous film, wherein the silicon precursor composition comprises a silylene compound selected from among:
(i) silylene compounds of the formula:

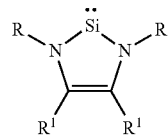

wherein each of R and R¹ is independently selected from
organo substituents;
(ii) amidinate silylenes; and
(iii) bis(amidinate) silylenes,
wherein when each R¹ is H, each R is not butyl.

9. The method of claim 8, further comprising annealing the HfSiO amorphous film to effect crystallization thereof.

10. The method of claim 9, wherein said annealing is conducted at temperature in a range of from 500° C. to 1200° C.

11. A method of making a ferroelectric field effect transistor, comprising:
forming a base comprising source and drain regions;
depositing on the base, in contact with the source and drain regions, an oxide layer;
forming on the oxide layer a HfSiO material by a vapor deposition process, using a silicon precursor composition, an organohafnium precursor, and an oxic medium in the vapor deposition process;
depositing a metal-containing layer on the HfSiO material; and
annealing the HfSiO material to form ferroelectric HfSiO material,
wherein the silicon precursor composition comprises a silylene compound selected from among:
(i) silylene compounds of the formula:

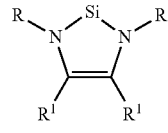

wherein each of R and R¹ is independently selected from
organo substituents;
(ii) amidinate silylenes; and
(iii) bis(amidinate) silylenes,
wherein when each R¹ is H, each R is not butyl.

12. The method of claim 11, wherein the oxide layer comprises $SiO_2$.

13. The method of claim 11, wherein the metal-containing layer comprises TiN.

14. The method of claim 11, wherein the organohafnium precursor comprises tetrakis-dialkylamino hafnium.

15. The method of claim 11, wherein the oxic medium comprises ozone.

16. The method of claim 11, wherein the annealing is carried out to form the ferroelectric HfSiO material comprising an orthorhombic phase.

17. A method of sealing porosity in a substrate comprising porous silicon oxide, comprising volatilizing a silicon precursor composition to produce corresponding precursor vapor, and contacting the precursor vapor with the substrate under vapor deposition conditions including (i) temperature in a range of from 50° C. to 200° C. and (ii) presence of oxidant, to deposit silicon oxide in said porosity of the substrate for sealing thereof, wherein the silicon precursor composition comprises a silylene compound selected from among:
(i) silylene compounds of the formula:

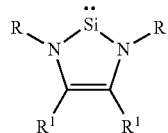

wherein each of R and $R^1$ is independently selected from organo substituents;
(ii) amidinate silylenes, and
(iii) bis(amidinate) silylenes,
wherein when each $R^1$ is H, each R is not butyl.

18. The method of claim 17, wherein the oxidant comprises water or ozone.

* * * * *